United States Patent
Edmeades et al.

(10) Patent No.: US 6,333,198 B1
(45) Date of Patent: Dec. 25, 2001

(54) COMPOUND AND ITS USE

(75) Inventors: Lorraine Mary Edmeades, Bishop's Statford; Nigel Arthur Griffith-Skinner, Dartford; Derek Anthony Hill, Sittingbourne; Graham Thronton Hill, Hertford; Terence William Packham, Dartford, all of (GB)

(73) Assignee: Glaxo Wellcome, Inc., Research Triangle Park, NC (US)

( * ) Notice: Subject to any disclaimer, the term of this patent is extended or adjusted under 35 U.S.C. 154(b) by 0 days.

(21) Appl. No.: 09/265,670

(22) Filed: Mar. 10, 1999

(30) Foreign Application Priority Data

Jun. 10, 1998 (GB) .................................................. 9812413

(51) Int. Cl.$^7$ .......................... G01N 33/00; G01N 30/90
(52) U.S. Cl. .................................. 436/96; 436/8; 436/91; 436/98; 436/161; 436/162; 514/242; 544/182
(58) Field of Search .......................... 514/242; 544/182; 436/8, 91, 96, 98, 161–162

(56) References Cited

U.S. PATENT DOCUMENTS

| | | |
|---|---|---|
| 4,486,354 | 12/1984 | Baxter et al. . |
| 4,560,687 | 12/1985 | Baxter et al. . |
| 4,602,017 | 7/1986 | Sawyer et al. . |
| 5,925,755 * | 7/1999 | Lee ........................................ 544/182 |
| 5,942,510 * | 8/1999 | Floyd et al. .......................... 514/242 |

FOREIGN PATENT DOCUMENTS

| | | |
|---|---|---|
| 0247892A1 | 12/1987 | (EP) . |
| WO 96/20934 | 7/1996 | (WO) . |

OTHER PUBLICATIONS

A. Fazio et al, Ther. Drug Monit. 1992, 14, 509–512, Jun. 1992.*
A. D. Fraser et al, Ther. Drug Monit. 1995, 17, 174–178, Feb. 1995.*
I. N. Papadoyannis et al, J. Liq. Chromatog. 1995, 18, 2593–2609.*
E. Dreassi et al, J. AOAC Int. 1996, 79, 1277–1280.*
E. Schmitt et al, J. Pharm. Sci. 1996, 85, 1215–1219, Nov. 1996.*
A. Bartoli et al, Ther. Drug Monit. 1997, 19, 100–107. Jan. 1997.*
T. K. Save et al, J. Chromatog. B 1997, 690, 315–319, Mar. 1997.*
B. C. Sallustio et al, Ther. Drug Monit. 1997, 19, 688–693, Jun. 1997.*
R. L. DeAngelis et al, J. Chtomatog. 1980, 221, 353–360, Dec. 1980.*
M. G. Quaglia et al, J. Chromatog. 1988, 456, 435–439, Dec. 1988.*
M. V. Doig et al, J. Chromatog. 1991, 554, 181–189.*
M. Cociglio et al, J. Chromatog. 1991, 572, 269–276.*
Sailstad et al Therapeutic Drug Monitoring Vol. 13,. No. 5, pp 433–442 (1991) Immunofluorometric Assay for Lamotrigine (Lamictal) in Human Plasma.
Londero et al. "New micromethod for the determination of lamotrigine. . . " Journal of Chromatography B. vol. 691, No. 1, pp. 139–144.
Dasgupta et al, "Lamotrigine anaylsis in plasma by gas chromatography–mas. . ." Journal of Chromatography B. vol. 693, No. 1, pp. 101–107.
Sailstad et al: Immunofluorometric Assay for Lamotrigine (Lamictal) in Human Plasma, "*Therapeutic Drug Monitoring*", 13:433–442, 1991.

* cited by examiner

*Primary Examiner*—Arlen Soderquist
(74) *Attorney, Agent, or Firm*—Nixon & Vanderhye

(57) ABSTRACT

A method of testing the purity or stability to degradation of a sample of lamotrigine or a pharmaceutical dosage form comprising lamotrigine comprises assaying the said sample for the presence of a compound selected from 3-amino-6-(2,3-dichlorophenyl)-1,2,4-triazine-5-(4H)-one (compound A) and N-[5-amino-6-(2,3-dichlorophenyl)-1,2,4-triazine-3-yl]-2,3-dichlorobenzamide (compound B). A process for producing compound B, which is novel, is also disclosed.

9 Claims, No Drawings

COMPOUND AND ITS USE

The present invention relates to compounds useful as reference markers for the analysis of lamotrigine and pharmaceutical formulations thereof.

In order to secure marketing approval for a new drug product, a drugs manufacturer must submit detailed evidence to the appropriate regulatory authority to show that the product is suitable for release on to the market. The regulatory authority must be satisfied, inter alia, that the active agent is acceptable for administration to humans and that the particular formulation which is to be marketed is free from impurities at the time of release and has an appropriate shelf-life.

Submissions made to regulatory authorities therefore typically include analytical data which demonstrate (a) that impurities are absent from the drug at the time of manufacture, or are present only at a negligible level, and (b) that the storage stability, i.e. shelf-life, of the drug is acceptable. These data are usually obtained by testing the drug against an external standard, or reference marker, which is a suitably pure sample of a potential impurity or a potential degradation product.

Potential impurities in pharmaceutically active agents and formulations containing them include residual amounts of synthetic precursors to the active agent, by-products which arise during synthesis of the active agent, residual solvent, isomers of the active agent, contaminants which were present in materials used in the synthesis of the active agent or in the preparation of the pharmaceutical formulation, and unidentified adventitious substances. Other impurities which may appear on storage include substances resulting from degradation of the active agent, for instance by oxidation or hydrolysis.

Lamotrigine is 3,5-diamino-6-(2,3-dichlorophenyl)-1,2,4-triazine, of formula (IV)

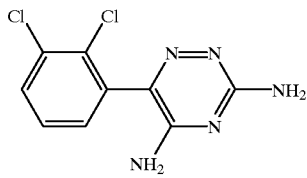

(IV)

It is a known compound which is useful in the treatment of disorders of the central nervous system (CNS), in particular epilepsy, as described for example in EP-A-0021121. Both lamotrigine per se and its pharmaceutical formulations are manufactured relatively free from impurities. In particular, lamotrigine remains stable during the manufacture of its pharmaceutical formulations.

It has now been appreciated that two compounds can be used as reference markers for the analysis of lamotrigine or of pharmaceutical dosage forms comprising lamotrigine. One of the compounds is a potential degradation product of lamotrigine and the other is a potential contaminant arising from side reactions during the synthesis of lamotrigine.

The present invention therefore provides a method of testing the purity or stability to degradation of a sample of lamotrigine or a pharmaceutical dosage form comprising lamotrigine, which method comprises assaying the said sample for the presence of a compound selected from 3-amino-6-(2,3-dichlorophenyl)-1,2,4-triazine-5-(4H)-one and N-[5-amino-6-(2,3-dichlorophenyl)-1,2,4-triazine-3-yl]-2,3-dichlorobenzamide. In the method of the invention the said compound is acting as a reference marker.

3-Amino-6-(2,3-dichlorophenyl)-1,2,4-triazine-5-(4H)-one is a compound of formula A:

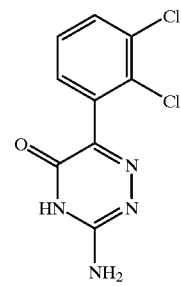

(A)

The compound of formula A (compound A) is a potential degradation product of lamotrigine which is produced upon hydrolysis of the drug. The compound of formula A may therefore be produced by hydrolysing lamotrigine under basic conditions. The hydrolysis is suitably conducted by combining lamotrigine and a base with water, and then heating the resulting solution under reflux. The base is preferably a strong base, for instance an alkali metal hydroxide. Sodium hydroxide is particularly preferred. The basic solution in water may be heated under reflux for a period of from 1 hour to 48 hours, for instance from 10 hours to 36 hours, preferably for 24 hours.

The other compound used as a reference marker is novel. The invention therefore provides a compound which is N-[5-amino-6-(2,3-dichlorophenyl)-1,2,4-triazine-3-yl]-2,3-dichlorobenzamide of formula B:

(B)

The compound of formula B (compound B) may be produced directly by treating lamotrigine with 2,3-dichlorobenzoyl chloride in pyridine. However, it has utility as a reference marker for lamotrigine because it is a potential contaminant arising from side reactions which can occur during the synthesis of the drug. In practice the level of this contaminant is controlled at a maximum of 0.5% in the crude lamotrigine by thin-layer chromatography (TLC). Recrystallisation of crude drug of this quality then results in the production of lamotrigine meeting the required purity level for commercial production of not more than 2% total impurities.

The synthesis of lamotrigine is illustrated in Reference Example 1. 2,3-Dichlorobenzoyl cyanide, which is intermediate 1.4 in that synthesis, may contain up to 10% of 2,3-dichlorobenzoic anhydride as a contaminant. When the 2,3-dichlorobenzoyl cyanide is treated with a solution of aminoguanidine bicarbonate in sulphuric acid, which is step (d) in Reference Example 1, the adduct (Z)-2-(2,3-dichlorophenyl)-2-(guanidinoimino)acetonitrile (intermediate 1.5) is produced. The anhydride contaminant can then react with the latter adduct to form (Z)-2-(2,3-dichlorophenyl)-2-[N'-(2,3-dichlorobenzoyl)guanidinoimino]acetonitrile, which is the direct precursor to compound B. Cyclisation of the precursor in propan-1-ol under reflux yields compound B.

The present invention therefore further provides a process for producing compound B, which process comprises
(i) reacting 2 equivalents of 2,3-dichlorobenzoyl chloride with 1 equivalent of lamotrigine dissolved in pyridine at a temperature of less than 35° C.; or
(ii) cyclising a compound of formula (I):

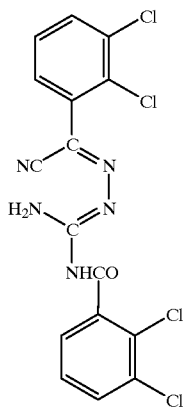

(I)

in propan-1-ol under reflux.

In step (ii), the compound of formula (I) is produced by reacting together compounds of formulae (II) and (III):

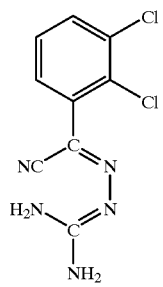

(II)

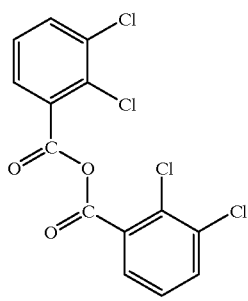

(III)

in the presence of a mineral acid, for instance sulphuric acid.

The compound of formula (II) is produced by treatment of 2,3-dichlorobenzoyl cyanide with a solution of aminoguanidine bicarbonate in sulphuric acid.

When compounds A and B are used as reference markers they must be in a suitably pure form. Compounds A and B produced as described above may be purified if necessary to achieve the desired purity level. The process of the invention for producing compound B as described above may therefore include the additional step of purifying the resulting compound.

Purification may be carried out by conventional methods which are routine in organic synthesis. For instance, the compound may be heated in an organic solvent such as a $C_1$–$C_6$ alkanol, filtered and dried under vacuum. Heating is typically carried out at the reflux temperature of the solvent. A $C_1$–$C_6$ alkanol is preferably propanol. Alternatively the compound may be recrystallised from a hot $C_1$–$C_6$ alkanol solvent, preferably hot propanol.

Compounds A and B are preferably finally recovered in substantially pure form. The purity level of a final sample of either compound is typically at least 80%, for example at least 85%, more preferably at least 90%. Purity levels above 90% may be desirable but are not essential. The purity level may be, for instance, at least 92%, at least 95% or at least 98%. Even more desirably the purity level is 99% or 99.5%.

Either lamotrigine itself (also referred to as drug substance) or a pharmaceutical dosage form comprising lamotrigine (also referred to as drug product) may be analysed for purity or stability to degradation. For instance, it is necessary to ensure that lamotrigine is pure following its manufacture. The drug substance is therefore typically assayed for both the degradation product (compound A) and the process impurity (compound B). Pharmaceutical dosage forms of lamotrigine need to be analysed to check that the active agent remains stable to degradation both during manufacture of the drug product and after several years' storage. Pharmaceutical dosage forms, which include conventional oral tablets and dispersible tablets, are therefore typically assayed for compound A only.

The test sample of drug substance or drug product to be analysed may be assayed by one or more conventional analytical techniques. The analytical techniques include high performance liquid chromatography (HPLC) and thin layer chromatography (TLC). The results obtained are compared with the results obtained from testing a substantially pure reference sample of compound A or B. The content of the or each compound in the test sample can then be determined.

In one aspect, the method of the invention is for testing the purity of a sample of lamotrigine, and includes the steps of:
(i) dissolving a sample of lamotrigine in a solvent to produce a sample solution;
(ii) dissolving a sample of 3-amino-6-(2,3-dichlorophenyl)-1,2,4-triazine-5-(4H)-one or N-(5-amino-6-(2,3-dichlorophenyl)-1,2,4-triazine-3-yl]-2,3-dichlorobenzamide in a solvent to product a reference marker standard solution;
(iii) subjecting the sample solution and the standard solution to thin layer chromatography to obtain a TLC chromatogram for each; and
(iv) estimating the intensity of any secondary spot obtained in the chromatogram of the sample solution, which corresponds in Rf value to the reference marker, against the spot due to the reference marker in the chromatogram of the standard solution.

In another aspect the method of the invention is for testing the stability to degradation of a pharmaceutical dosage form comprising lamotrigine, and includes the steps of:
(i) dissolving a sample of the dosage form in a solvent to produce a sample solution;

(ii) dissolving a sample of 3-amino-6-(2,3-dichlorophenyl)-1,2,4-triazine-5-(4H)-one in a solvent to produce a reference marker standard solution;

(iii) subjecting the sample solution and the standard solution to thin layer chromatography to obtain a TLC chromatogram for each; and (iv) estimating the intensity of any secondary spot obtained in the chromatogram of the sample solution, which corresponds in Rf value to the reference marker, against the spot due to the reference marker in the chromatogram of the standard solution.

In a further aspect the method of the invention is for testing the stability to degradation of a pharmaceutical dosage form comprising lamotrigine, and includes the steps of:

(i) dissolving a sample of the dosage form in a solvent to produce one or more sample solutions;

(ii) dissolving a sample of lamotrigine reference standard in a solvent to produce a standard solution;

(iii) injecting the sample and standard solutions on to an HPLC column, and (iv) determining the main peak areas of each solution and calculating from these the content of the reference marker compound 3-amino-6-(2,3-dichlorophenyl)-1,2,4-triazine-5-(4H)-one in the sample solution.

In this further aspect it may be necessary to run a system suitability solution through the HPLC column prior to step (iii) in order to determine the resolution factor between lamotrigine and any formulation excipients present in the pharmaceutical dosage form. In that case the method includes the additional step of:

(iia) dissolving lamotrigine and the formulation excipient reference standards in a solvent to produce an HPLC system suitability solution, and injecting the system suitability solution on to the HPLC column to determine the resolution factor between lamotrigine and the formulation excipient. The formulation excipient may, for instance, be saccharin sodium.

The invention also provides the use of a compound selected from 3-amino-6-(2,3-dichlorophenyl)-1,2,4-triazine-5-(4H)-one and N-[5-amino-6-(2,3-dichlorophenyl)-1,2,4-triazine-3-yl]-2,3-dichlorobenzamide as a reference marker in analysing the purity or stability to degradation of a sample of lamotrigine or a sample of a pharmaceutical dosage form comprising lamotrigine.

In practice lamotrigine is relatively pure and is quite stable on storage. Analytical testing of the drug substance itself, or of pharmaceutical dosage forms containing lamotrigine, therefore serves principally to confirm that compounds A and/or B are absent or are present only at levels below the limit of detection for the analytical technique in question (about 0.3% w/w for TLC and 0.06% w/w for HPLC).

As an alternative to assaying a sample of the reference marker separately each time it is desired to assess data obtained from analysing a sample of drug substance or drug product, a parameter known as the Response factor (R) may instead be used. A Response factor is a previously determined ratio of a numerical result obtained by testing a sample of compound A or B using a given analytical technique, to the corresponding numerical result obtained by testing pure lamotrigine at an equivalent concentration. The numerical result in question may be, for instance, an HPLC peak area response value. Thus, given appropriate analytical results for pure lamotrigine and for a test sample of a pharmaceutical dosage form of lamotrigine, the known Response factor for compound A or B can be used to calculate the amount of that particular reference marker in the test sample.

The calculation may be illustrated with reference to HPLC analysis results as follows:

$$\frac{\% \text{ w/w of compound } A \text{ or } B \text{ in}}{\text{test sample relative to lamotrigine}} = \frac{Ar \times Ws}{As \times R}$$

wherein:

Ar=main peak area of the compound in HPLC test solution

As=main peak area of lamotrigine alone in HPLC standard solution

R=Response factor of the compound

Ws=weight (in mg) of the standard taken

For compound A of the invention the HPLC Response factor is 0.79.

The invention will be further described in the Examples which follow.

REFERENCE EXAMPLE 1

Preparation of Lamotrigine

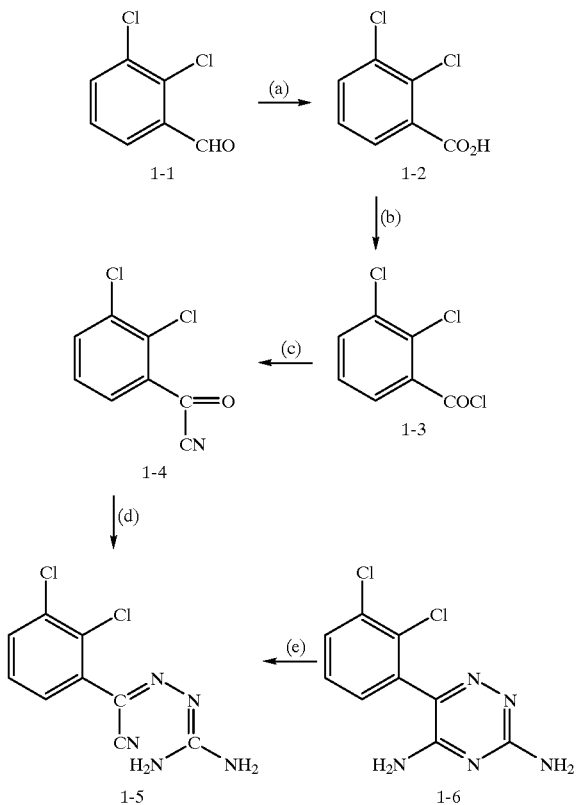

Step a: Preparation of 1.2

A solution of 1.1 (1 mole), tertiary-butyl alcohol, water and sodium hydroxide (2 moles) was stirred and hydrogen peroxide solution (35% w/w, 4 moles) was added at 50–60° C. over 3 hours. After stirring at 55–60° C. for 30 minutes, the tertiary-butyl alcohol was removed by distillation and the aqueous solution was washed with toluene. The aqueous solution was acidified to pH 1–2, and the product was filtered and washed with water. The damp solid was either used directly in the next stage of the process or dried at 80–90° C. to afford a white solid in 75% yield.

Steps (b) and (c): Preparation of 1.4

A solution of 1.2 (1 mole) in toluene was stirred and dried by distillation. It was then cooled and pyridine (0.005 moles) was added, followed by a slow addition of thionyl chloride (1.1 moles). The solution was heated under reflux for 1 hour, then concentrated in vacuo to afford crude 1.3. Potassium iodide (1.2 moles) was added, followed by cuprous cyanide (1.2 moles) and any remaining solvent was removed by distillation until the internal temperature was 140–144° C. This temperature was maintained for 18–24 hours, then the reaction mixture was cooled, diluted with toluene and filtered to remove inorganic salts. The solution was evaporated to dryness in vacuo at 60–70° C., and the residual oil crystallised from petroleum ether to yield 1.4 as a yellow solid in 77% yield.

Step d: Preparation of 1.5

Aminoguanidine bicarbonate (1.75 moles) was dissolved in 9.3–10.0 M sulphuric acid solution. A solution of 2,3-dichlorobenzoyl cyanide (1 mole) in acetonitrile was added and the suspension stirred at 20–30° C. for 42–48 hours. The crude product was filtered and washed with water. The solid was added to sodium hydroxide solution below 35° C., then the product was filtered, washed with water and dried at 80–90° C. to obtain 1.5 as a yellow solid in 66% yield.

Step (e) Preparation of Crude Lamotrigine

A solution of 1.5 in propan-1-ol was stirred under reflux for 90–120 minutes, cooled to 15–25° C. and crude lamotrigine was filtered to obtain a pale brown solid in a 90% yield (on a dry basis). The crude lamotrigine was purified by recrystallisation from propan-1-ol, using charcoal, and cooling the solution to 15–25° C. The solid was filtered, washed with propan-1-ol and dried at 80–90° C. to afford pure lamotrigine.

EXAMPLE 1

Preparation of 3-amino-6-(2,3-dichlorophenyl) -1,2,4-triazine-5(4H)-one (Compound A)

Lamotrigine (614.4 g, 2.4 moles) and solid sodium hydroxide (242.4 g) were combined with water (60 l) and refluxed with stirring for 24 hours. The resulting solution was cooled to 15–20° C. and the pH adjusted to from 5.5 to 6.0 with hydrochloric acid. The resulting solid was filtered and dried for 24 hours, first at 40° C., then at 50° C. and finally at 70° C. The purity of the product was determined by HPLC as 82%. The HPLC conditions were as follows:

Column: Spherisorb 50 DS
Eluent: Water (600): Acetonitrile (400): 0.5M
Sulphuric acid (15)
Flow rate: 2.0 ml/min
Sample: 50 mg in 100 ml
Inject: 5 or 10 µl
Detection: 270 nm A sample of the 82% pure product (583 g) was combined with propanol (15l) and refluxed for 0.5 hours. Following extraction and drying, compound A was obtained in 96.2% pure form as determined by HPLC, using the conditions described above.

A further purification step was performed by refluxing a sample of 96.2% pure product in propanol (5l) for 1 hour, with stirring. The solid was filtered and dried at 40° C. under vacuum to afford the title compound (460.7 g, 74.7% yield). The final product had a purity of 99.1% as determined by HPLC.

The product had the following physical characteristics:
Molecular formula: $C_9H_6Cl_2N_4O$ Molecular mass: 257.08

| | Elemental analysis | | |
|---|---|---|---|
| | C | H | N |
| calc | 42.06% | 2.35% | 21.80% |
| found | 42.02% | 2.25% | 21.23% |

TLC (silica gel with Chloroform:Methanol:Glacial acetic acid:Butan-1-ol 80:10:10:5)

main spot at Rf=0.38
trace at Rf=0.82

Infra-red (KBr): $V_{max}$ ($cm^{-1}$): 3301, 3127, 1655 1556, 1484, 1413, 1290, 1200, 1056 812, 785, 748 737, 719

$^1$H nmr: δ/ppm in $d_6$-dmso (22 mg $ml^{-1}$)/300 MHz: 12.43 (1H,bs); 7.71, 7.68 (1H,m); 7.40 (2H,m); 6.99 (2H,bs); 3.3 (bs(water)); 2.5 (q(dmso-$d_5$)); 0 (s,TMS).

Mass spec: m/z: 256 ($M^+$), 258 and 260 (associated isotope ions), 221, 186, 171, 85 (fragment ions as indicated below:)

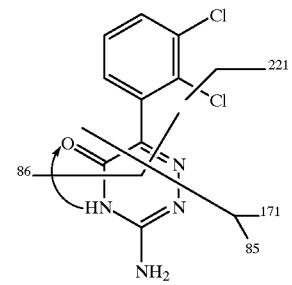

EXAMPLE 2

Preparation of N-[5-Amino-6-(2,3-dichlorophenyl)-1,2,4-triazine-3-yl]-2,3-dichlorobenzamide (Compound B)

Lamotrigine (512.00 g, 2.00 moles) was dissolved in pyridine (3 l) and 2,3-dichlorobenzoyl chloride (873.00 g, 96% pure, equivalent to 838.10 g, 4.00 moles) was added below 35° C. with stirring under anhydrous conditions. The acid chloride was added in two equal portions. The second portion of acid chloride was added after 30 minutes from the start of the reaction and stirred below 35° C. for a further 30 minutes.

The resulting mixture was concentrated to almost dryness and then triturated with chloroform (1300 ml) for 10 minutes with stirring. The resulting solid was filtered and washed with chloroform (3×50 ml) and dried at room temperature to a weight of 308 g, 36% (based on compound B). A sample of the crude product (50.0 g) was heated with methanol (500 ml) at reflux temperature with stirring for 1 hour and the resulting hot mixture was filtered to afford compound B in very pure form (37.0 g).

The product has the following physical characteristics:
Molecular formula: $C_{16}H_9Cl_4N_5O$ Molecular mass: 429.09

Infra-red (KCl): $v_{max}(cm^{-1})$: 3468, 3300, 3202, 3385, 3277, 1687, 1625, 1559, 1414, 1387, 1538, 1459, 1253, 1157, 1136, 1116, 790, 775, 741, 724

$^1$H nmr: δ/ppm in d$_6$-dmso (39 mg ml$^{-1}$)/300 MHz: 10.85 (1H, bs); 7.8 (1H, bs); 7.1 (1H, bs); 7.77 (1H, d, J=7 Hz); 7.73(1H,d,J=7 Hz); 7.5 (4H, m); 4.08(bs); 3.32 (bs, water); 3.18 (s); 2.50 (quintet, dmso-d$_5$); 2.31 (s, methane sulphonate); 0.00 (s, TMS).

Mass spectroscopy

Chemical ionisation (CI): m/z: 428 (M+1)$^+$; 430, 432 and 434 (associated isotope ions).

Electron impact (EI): m/z: 428 (m+1)$^+$; 392,199,185,173, 145 (fragment ions as indicated below:)

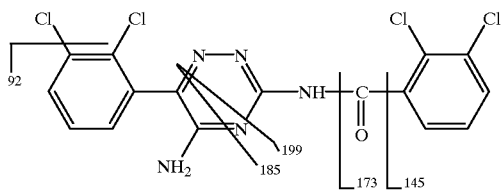

EXAMPLE 3

Assay for Lamotrigine and Compound A in Drug Product (Dispersible Tablets) by HPLC Preparation of Standard and System Suitability Solutions A standard solution was prepared by transferring lamotrigine reference standard (approximately 100 mg, accurately weighed) into a 500 ml volumetric flask. Methanol (200 ml) was added to dissolve the solid, followed by hydrochloric acid (100 ml, 0.5M) with mixing. The resulting solution was allowed to cool to room temperature and diluted to volume with water.

A system suitability solution was prepared by transferring lamotrigine reference standard (100 mg) and saccharin sodium reference standard (20 mg) to a 500 ml volumetric flask and diluting to volume with water.

Preparation of Sample Solutions

Solution S1

From the information given in table 1 which follows, solution S1 was prepared by transferring the specified number of tablets to the specified volumetric flask. The specified volume of hydrochloric acid (0.5 M) was added is and the solution swirled until the tablets had disintegrated and the resulting effervescence had ceased.

The specified volume of methanol was added and the solution was placed in an ultrasonic bath for 10 minutes. The solution was then allowed to equilibrate to ambient temperature and diluted to volume with water.

TABLE 1

| Tablet Strength | Number of Tablets | Volumetric Flask Size (ml) | 0.5 M Hydrochloric Acid Volume (ml) | Methanol Volume (ml) |
|---|---|---|---|---|
| 5 mg | 10 | 250 | 50 | 100 |
| 25 mg | 8 | 200 | 40 | 80 |
| 50 mg | 5 | 250 | 50 | 100 |
| 100 mg | 5 | 500 | 100 | 200 |
| 200 mg | 5 | 1000 | 200 | 400 |

Solution S2 a) 5 mg tablets

Solution S1, prepared as described above, was filtered through a Whatman No. 1 filter paper. The first 10 ml of filtrate was discarded. The clear filtrate was the sample solution.

b) 25 mg, 50 mg, 100 mg and 200 mg Tablets

Solution S1 was filtered through a Whatman No. 1 filter paper. The first 10 ml of filtrate was discarded. The filtrate (10.0 ml) was transferred into a 50 ml volumetric flask and was diluted to volume with a mixture of hydrochloric acid (0.5 M): water: methanol (20:20:40 v/v).

Chromatographic Procedure

The following conditions were used:

Column: 125×4.6 mm (i.d.) Stainless steel packed with Spherisorb 5 μm ODS 1 or validated equivalent Mobile phase: Water/methanol/acetonitrile/glacial acetic acid/n-octylamine (700/100/100/20/0.5 v.v)

Temperature: Ambient

Flow rate: 2.0 ml//minute

Wavelength: 275 nm

Injection volume: 20 μl

Notes:

(a) Columns were conditioned before use by pumping through methanol at a low flow rate for about 30 minutes.

(b) The specificity was influenced by the ratio of water to methanol:acetonitrile.

(c) Decreasing the methanol: acetonitrile content of the mobile phase increases the resolution of lamotrigine and sodium saccharin; the retention time of all components is also increased.

(d) Minor changes in acid concentrate methanol to acetonitrile ratio and acetylamine levels had no significant impact on the chromatographic specificity.

(e) After use the column was washed with methanol: water (1.9) followed by methanol.

Injection Procedure

When a stable baseline was obtained the system suitability solution was injected and the resolution factor between lamotrigine and saccharin sodium was calculated. The symmetry factor and number of theoretical plates for lamotrigine were also calculated using General Method of the European Pharmacopoeia for Calculating System Suitability Parameters).

The values obtained were as follows:

Resolution 10

Symmetry factor 1.2

No. of theoretical plates 1400

The standard solution and sample solution S2 were then injected onto the column.

Calculations

From the main peak area of the standard solution the response factor (R) for lamotrigine was calculated as follows:

$$R = \frac{Ws \times P}{As \times 100}$$

where:

Ws=weight (mg) of lamotrigine standard taken

P=% purity of lamotrigine reference standard

As=area of lamotrigine peak in standard solution injection

The mean response factor (MR) was used to calculate the lamotrigine content of the sample as follows:

$$\text{Lamotrigine content (mg/tablet)} = \frac{Au \times MR \times DFu}{DFs \times N}$$

$$\text{Lamotrigine content} \atop (\% \text{ of label claim}) = \frac{Au \times MR \times DFu \times 100}{DFs \times N \times L}$$

where:
Au=area of lamotrigine peak in sample solutions S2 injection
N=number of tablets tested
DFs=dilution factor for standard solution (500)
DFu=dilution factor for sample solution (250 for 5 mg tablets, 1000 for 25 mg tablets, 1250 for 50 mg tablets, 2500 for 100 mg tablets and 5000 for 200 mg tablets).
L=label claim
The content of any secondary component eluting at the retention time of compound A was calculated with respect to the standard lamotrigine as follows:

$$\text{Compound } A \text{ content (w/w)} \atop \text{with respect to lamotrigine} = \frac{Ai \times Ws}{As \times 0.79}$$

where
Ai=area of peak for compound A in sample solution S2 injection
Ws=weight (mg) of lamotrigine reference standard taken
As=area of lamotrigine peak in standard solution injection
0.79 - relative response factor for compound A
Similarly the level of any other lamotrigine related secondary components was calculated on a % w/w basis assuming a relative response factor of 1.0. The following results in Table 2 were obtained:

TABLE 2

| Component | Retention Time (minutes) | Relative Retention Time | Relative Response Factor (RRF) |
|---|---|---|---|
| Compound A | 5.5 | 3.9 | 0.79 |
| Lamotrigine | 1.4 | 1.0 | 1.0 |
| Blackcurrant flavour | 2.5 | 1.8 | — |
| Saccharin sodium | 3.2 | 2.3 | — |

EXAMPLE 4

Determination of Compounds A and B in Drug Substance (Lamotrigine, 125 μm Particle Size) by TLC Test 1—compound B
The following standard and test solutions were prepared in an equivolume mixture of methanol and 2-methoxyethanol:
solution 1: 5.0% w/v solution of the sample
solution 2: 5.0% w/v solution of lamotrigine reference sample
solution 3: 0.02% w/v solution of compound B
solution 4: 1.0 ml of solution 2 diluted to 250 ml
solution5: 10.0 ml of solution 4 diluted with 10.0 ml of solution 3
solution 6: 7.5 ml of solution 5 diluted to 10.0 ml
solution 7: 5.0 ml of solution 5 diluted to 10.0 ml
solution 8: 2.5 ml of solution 5 diluted to 10.0 ml
The following TLC operating conditions were used:
plate: 20×20 cm plate coated with a 0.25 mm layer of Silica gel 60 $F_{254}$
mobile phase: ethyl acetate/glacial acetic acid/methanol (85:10:5 v/v)
spot loading: 10 μl of each solution
length of run: 10 cm
The TLC plate was allowed to dry in air and was then viewed under ultra-violet light at 254 nm. The test was not valid unless the chromatogram obtained with solution 5 exhibited two clearly separated spots and the corresponding spots in the chromatogram from solution 8 were both detectable.
The intensity of any secondary spot corresponding in $R_f$ value to compound B obtained in the chromatogram of solution 1 against the spots due to compound B obtained in the chromatograms of solutions 5, 6, 7 and 8 (equivalent to 0.2, 0.15, 0.1 and 0.05% w/w, respectively) was estimated.
The intensity of any secondary spots obtained in the chromatogram of solution 1 against the spots due to lamotrigine obtained in the chromatograms of solutions 5,6,7 and 8 (equivalent to 0.2, 0.15, 0.1 and 0.05%, respectively) were estimated.
The Rf values obtained were: lamotrigine: 0.20 compound B: 0.60
Test 2—compound A
The following test and standard solutions were prepared in an equivolume mixture of methanol and 2-methoxyethanol.
solution 1: solution 1 from Test 1 above
solution 2: 0.05% w/v solution of compound A
The following TLC operating conditions were used:
plate: 20 cm×20 cm plate coated with a 0.25 mm layer of Silica gel 60 $F_{254}$
mobile phase: chloroform/methanol/glacial acetic acid/butan-1-ol (80:10:10:5 v/v)
spot loading: 10 μof solution 1 μl and 2 μl of solution 2
length of run: 15 cm
The plate was allowed to dry in air and then viewed under ultra-violet light at 254 nm. The intensity of any secondary spot of corresponding $R_f$ value in the chromatogram of solution 1 against the spots due to compound A in solution 2 (equivalent to 0.1 and 0.2% w/w) was estimated.
The $R_f$ values obtained were:
lamotrigine: 0.25
compound A: 0.37

EXAMPLE 5

Determination of Compound A in Drug Product (100 mg Lamotrigine Tablets) by TLC
Preparation of Standard and Sample Solutions
A standard solution was prepared by accurately weighing about 10 mg of compound A into a 100 ml volumetric flask. The compound was dissolved in, and diluted to volume with, methanol.
A sample solution was prepared by transferring an amount of powdered tablets, equivalent to 500 mg of lamotrigine, into a 50 ml volumetric flask. The powder was dispersed in 15 ml of hydrochloric acid (0.1M) and a mixture of methanol:2-methoxyethanol (15/15 v/v, 30 ml) was added. The flask was placed in a ultrasonic bath for 10 minutes. The solution was then allowed to cool to ambient temperature and diluted to volume with the methanol:2-methoxyethanol solvent mixture. The solution was mixed well and filtered through filter paper (Whatman No. 1). The clear filtrate was the test solution.

Test Method

The following TLC operating conditions were used:

Plate: 20×20 cm plate, coated with a 0.25 mm layer of silica gel 60 $F_{254}$

Mobile phase: Chloroform/methanol/glacial acetic acid/butan-1-ol (80:10:10:5 v/v)

Spot loading: 10 μl of test solution, 3 μl and 5 μl of standard solution

Length of run: 15 cm

The plate was allowed to dry in a current of air and was viewed under ultraviolet light at 254 nm.

The intensity of any spot other than the main spot obtained in the chromatogram of the sample solution against the spot obtained with 3 μl of the standard solution (corresponding to 0.3 % w/w impurity) was estimated. The combined intensity of all secondary spots was not greater than the 5 μl loading of the standard solution (corresponding to 0.3% w/w impurity).

The Rf values were as follows:

Lamotrigine: 0.20

Compound A: 0.34

Throughout this specification and the appended claims it is to be understood that the words "comprise" and "include" and variations such as comprises, "comprising", "includes", "including" are to be interpreted inclusively, unless the context requires otherwise. That is, the use of these words may imply the inclusion of an element or elements not specifically recited.

The present invention has been described by way of example only, and it is to be recognised that modifications thereto which fall within the scope and spirit of the appended claims, and which would be obvious to a skilled person based upon the disclosure herein, are also considered to be included within the invention.

What is claimed is:

1. A method of testing the purity of a sample of lamotrigine or a pharmaceutical dosage form comprising lamotrigine, which method comprises assaying the said sample for the presence of N-[5-amino-6-(2,3-dichlorophenyl)-1,2,4-triazin-3-yl]-2,3-dichlorobenzamide.

2. A method according to claim 1 for testing the purity of a sample of lamotrigine, which includes the steps of:

(i) dissolving a sample of lamotrigine in a solvent to product a sample solution;

(ii) dissolving a sample of N-(5-amino-6-(2,3-dichlorophenyl)-1,2,4-triazin-3-yl]-2,3-dichlorobenzamide in a solvent to produce a reference marker standard solution;

(iii) subjecting the sample solution and the standard solution to thin layer chromatography to obtain a TLC chromatogram for each; and (iv) estimating the intensity of any secondary spot obtained in the chromatogram of the sample solution, which corresponds in Rf value to the reference marker, against the spot due to the reference marker in the chromatogram of the standard solution.

3. A method of testing the purity of a sample of lamotrigine or a pharmaceutical dosage form comprising lamotrigine according to claim 1, which method further comprises using a sample of N-2,3-dichlorobenzamide having a purity level of at least 80% as a reference marker.

4. A compound which is N-[5-amino-6-(2,3-dichlorophenyl)-1,2,4-triazine-3-yl)]-2,3-dichlorobenzamide of formula (B):

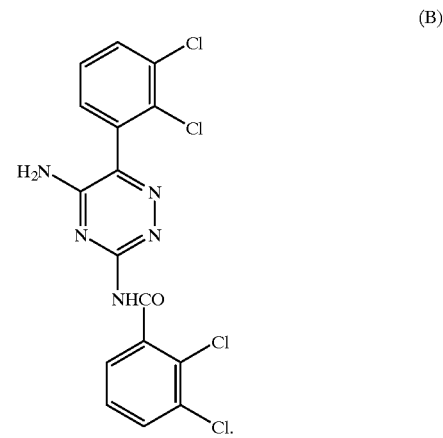

(B)

5. A sample of a compound as claimed in claim 4 which is in substantially pure form.

6. A sample according to claim 5 which has a purity level of 90% or above.

7. A process for producing a compound as defined in claim 4, which process comprises:

(i) reacting 2 equivalents of 2,3-dichlorobenzoyl chloride with 1 equivalent of lamotrigine dissolved in pyridine at a temperature of less than 35° C.; or (ii) cyclising a compound of formula (I):

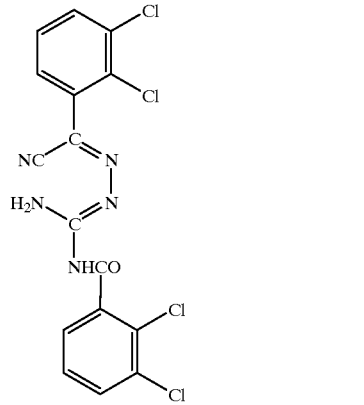

(I)

in propan-1-ol under reflux.

8. A process according to claim 7 wherein, in step (ii), the compound of formula (I) is produced by reacting together compounds of formulae (II) and (III):

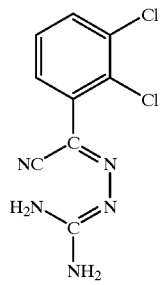

(II)

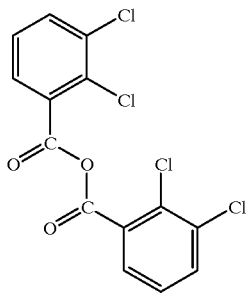

(III)

in the presence of a mineral acid.

9. A process according to claim 8 wherein the compound of formula (II) is produced by treatment of 2,3-dichlorobenzoyl cyanide with a solution of aminoguanidine bicarbonate in sulphuric acid.

* * * * *